United States Patent [19]

Maggio

[11] 4,277,437

[45] * Jul. 7, 1981

[54] KIT FOR CARRYING OUT CHEMICALLY INDUCED FLUORESCENCE IMMUNOASSAY

[75] Inventor: Edward T. Maggio, Redwood City, Calif.

[73] Assignee: Syva Company, Palo Alto, Calif.

[*] Notice: The portion of the term of this patent subsequent to Sep. 2, 1997, has been disclaimed.

[21] Appl. No.: 101,935

[22] Filed: Dec. 10, 1979

Related U.S. Application Data

[63] Continuation of Ser. No. 893,910, Apr. 5, 1978, Pat. No. 4,220,450.

[51] Int. Cl.³ ...................... G01N 33/54; G01N 33/58
[52] U.S. Cl. .................................. 422/61; 23/230 B; 23/915; 252/408; 424/8; 424/12; 435/7; 435/8; 435/810
[58] Field of Search ....................... 23/230 B; 422/61; 424/8, 12; 435/7, 810

[56] References Cited

U.S. PATENT DOCUMENTS

| | | | |
|---|---|---|---|
| 4,011,219 | 3/1977 | Nishii | 544/237 |
| 4,104,029 | 8/1978 | Maier, Jr. | 23/230 B |
| 4,181,650 | 1/1980 | Maier, Jr. | 424/12 X |
| 4,225,485 | 9/1980 | Buckler | 23/230 B X |

*Primary Examiner*—Sidney Marantz

*Attorney, Agent, or Firm*—Bertram I. Rowland

[57] ABSTRACT

A competitive protein binding method is provided for the determination of an analyte which is a member of an immunological pair consisting of ligand and receptor for the ligand. A chemiluminescent source is employed comprised of one or more individual members, one chemiluminescent source member being conjugated to one of the members of the immunological pair, so as to provide chemiluminescence adjacent to the site of conjugation. A quencher molecule is conjugated to a member of the immunological pair. When the members of the immunological pair bind, the quencher molecule is brought within quenching distance of the chemiluminescent source so as to inhibit the emission of light by the chemiluminescent source. The amount of analyte present in the assay medium affects the amount of binding between the members of the immunological pair which results in quenching of the chemiluminescence. By observing the light emitted from the assay medium, either from the chemiluminescent source or the quencher, the change in light emission in relation to the concentration of analyte present in the assay medium can be used to determine the amount of analyte present in the assay medium. By employing standards having known amounts of analyte, the amount of analyte in an unknown sample can be quantitatively determined.

Reagent kits can be provided having predetermined amounts of the reagents, so as to substantially optimize the sensitivity of the assay.

4 Claims, No Drawings

KIT FOR CARRYING OUT CHEMICALLY INDUCED FLUORESCENCE IMMUNOASSAY

CROSS-REFERENCE TO RELATED APPLICATIONS

This is a continuation of application Ser. No. 893,910, filed Apr. 5, 1978 now U.S. Pat. No. 4,220,450.

BACKGROUND OF THE INVENTION

1. Field of the Invention

The clinical diagnostic field has seen a broad expansion in recent years, both as to the variety of materials which may be readily and accurately determined, as well as the methods for the determination. One broad category of techniques involves the use of an organic receptor which is able to specifically bind to a particular spatial and polar organization of another molecule. For the most part, these compounds are antibodies, which are able to distinguish between the compound or composition of interest, and other compounds of analogous structure. By virtue of the binding of the receptor to a labeled ligand, one is able to distinguish between labeled ligand which is bound to receptor and unbound labeled ligand.

The observed effect of binding by the receptor will depend upon the label. In some instances, the binding of the antibody merely provides for a differentiation in molecular weight between bound and unbound labeled ligand. In other instances, the presence of the receptor may affect the nature of the signal obtained from the label, so that the signal varies with the amount of receptor bound to labeled ligand. A further variation is that the receptor is labeled and the ligand unlabeled. Where receptors are labeled with two different labels which interact when in close proximity, the amount of ligand present affects the degree to which the labels on the receptor may interact.

In developing an assay, there are many considerations. One consideration is the signal response to changes in the concentration of analyte. A second consideration is the ease with which the protocol for the assay may be carried out. A third consideration is the variation in interference from sample to sample. Ease of preparation and purification of reagents, availability of equipment, ease of automation, and interaction with ligands, are additional considerations, which do not exhaust the various concerns in developing a useful assay.

There is therefore a continuing need for new and accurate techniques which can be adapted for a wide spectrum of different ligands or be used in specific cases where other methods may not be readily adaptable.

2. Brief Description of the Prior Art

U.S. Pat. No. 3,709,868 is exemplary of a radioimmunoassay. U.S. Pat. No. 3,960,834 is exemplary of a spin immunoassay. U.S. Pat. No. 3,654,090 and German Auslegungsschrift No. 2,223,385 are exemplary of enzyme immunoassays. Articles of interest include an article by Ludwig Brand and James R. Gohlke, *Annual Review of Biochemistry*, 41, 843–868 (1972) and Stryer, *Science*, 162, 526 (1968). Smith, *FEBS Letters* 77, 25, (1977) describes a fluorescent immunoassay, where thyroxine is bound to a fluorescer and quenches the fluorescer, the quenching being reversed by binding of antibody to thyroxine. See also, Ullman et al, *J. Biol. Chem.* 251, 4172 (1976).

An excellent review of chemiluminescence may be found in McCapra, *Quarterly Reviews* 20, 485 (1966).

SUMMARY OF THE INVENTION

A competitive protein binding assay is provided having as an analyte a member of an immunological pair which consists of ligand and receptor for the ligand. The assay is predicated on the presence of the analyte in an assay medium affecting the degree to which a chemiluminescence source is quenched by energy transfer to a quencher, at relatively long distances. By conjugating the chemiluminescence source or where the chemiluminescence source requires a plurality of components, one component of the chemiluminescence source, with a member of the immunological pair and conjugating a quencher with a member of the immunological pair, reagents can be prepared which when combined in the assay medium will provide varying degrees of light emission, depending upon the amount of analyte present in the assay medium.

In particular, the chemiluminescence source or component thereof and the quencher may be conjugated to either the ligand or the receptor and the resulting reagent combined in an aqueous, normally buffered medium at a mild temperature, and the amount of light emitted determined. By comparison with assay media having known amounts of analyte, a quantitative relationship can be developed between the quanta of emitted light and the amount of analyte in the assay medium.

Kits can be provided, where the reagents are included in premeasured amounts, so that they may be used directly or may be readily diluted to assay reagent solutions to provide concentrations which substantially optimize the sensitivity and performance of the assay.

DESCRIPTION OF THE SPECIFIC EMBODIMENTS

In accordance with the subject invention, chemiluminescence is employed to provide a signal related to the amount of analyte in an assay medium. The analyte is a member of an immunological pair which includes ligand and receptor. By conjugating the chemiluminescence source or where the source is comprised of more than one component, one component of the chemiluminescence source, with a member of the immunological pair and a quencher with a member of the immunological pair, the presence of analyte affects the amount of quencher which is within quenching distance of the conjugated chemiluminescence source. By combining the chemiluminescence source reagent and the quencher reagent where the two labels are on different molecules, and additional immunological pair members, as required, with the analyte in an assay medium, including any ancillary reagents necessary for the chemiluminescence, and determining the amount of light emitted from the assay medium, at a particular wavelength or a range of wavelengths from the assay medium, in relation to an assay medium having a known amount of analyte, the amount of analyte in the sample can be determined.

The method is predicated on the observation that when a dye is within a limited distance from a chemiluminescer in the excited state, the chemiluminescer may transfer its energy to the quencher without collision and without emitting radiation. The quencher may then emit radiation of a higher wavelength than the chemiluminescer or may lose the energy by radiationless decay. One can conjugate the member of the chemiluminescence source and the quencher to either ligand or receptor, so that when the two conjugates are brought together the amount of quencher within quenching distance of the chemiluminescer is affected by the amount of analyte present in the assay medium. The nature and amount of light emitted from the assay medium will therefore be a function of the analyte present in the assay medium. By performing assays with known amounts of analyte, one can develop a quantative relationship between the amount of analyte in the assay medium and the amount of radiation emitted from the assay medium at one or more wavelengths.

Definitions

Analyte—the compound or composition to be measured, which may be a ligand which is mono- or polyepitopic, antigenic or haptenic, a single or plurality of compounds which share at least one common epitopic site or a receptor.

Ligand—any compound for which a receptor naturally exists or can be prepared.

Ligand analog—a modified ligand which can compete with the analogous ligand for receptor, the modification providing means to join to a label or to a hub nucleus.

Poly(ligand analog)—a plurality of ligand analogs joined together convalently, normally to a hub nucleus, to provide a compound having a plurality of epitopic sites capable of competing with the analogous ligand for receptor.

Label—either a component of a chemiluminescence source or a quencher dye, which form a light emitting reciprocal pair, where the quencher dye has a high transition probability of absorbing energy from the chemiluminescence source.

(a) chemiluminescer label—a compound which by itself or in combination with other compounds produces a molecule in an electronically excited state, which molecule can decay to a lower energy state by the emission of light and the total process results in a chemical change in one or more of the compounds.

(b) quencher—a molecule capable of inhibiting the chemiluminescent emission of light, when within a short but non-colliding distance, usually less than about 100 Å, of the chemiluminescer molecule, by accepting the energy which would otherwise be emitted as chemiluminescent light. In effect, the quencher need not be the nearest neighbor to the chemiluminescer to effect quenching.

Label-conjugate—the label, either a compound of the chemiluminescence source or the quencher, is bonded, either by a bond or linking chain, to a member of the immunological pair but not both to the same molecule. The conjugate will have at least one label and may have a plurality of labels bonded to the member of the immunological pair or a plurality of such members bonded to the label or a plurality of ligands and labels i.e. poly(ligand analog)-polylabel. In particular, where an enzyme is the component of the chemiluminescence source employed as the label, a plurality of ligand analogs may be conjugated to the enzyme to form a poly(ligand analog) label.

Receptor—any compound or composition capable of recognizing a particular spatial and polar organization of a molecule i.e. epitopic site. Illustrative receptors include naturally occurring receptors, antibodies, enzymes, lectins, Fab fragments and the like. The receptor may be monovalent or polyvalent in receptor sites usually polyvalent e.g. antibodies. For any specific ligand, the receptor will be referred to as "antiligand". The receptor-antiligand-and its reciprocal ligand form an immunological pair.

Poly(ligand analog)-label—a composition in which a plurality of ligand analogs and one or a plurality of labels are bonded together whereby the ligand analog and label are in juxtaposition, so that when receptor is bound to ligand analog, label on the labeled receptor is in within quenching distance of the reciprocal label. Where an enzyme is part of the chemiluminescence source and the ligand is haptenic, a plurality of ligand analogs may be bonded to the enzyme. Alternatively, a plurality of ligand analogs and one or more labels may be conjugated to a water soluble polyfunctionalized hub nucleus.

Assay

The subject assay is carried out in an aqueous, normally homogeneous, zone normally, but not necessarily at a moderate pH, generally close to optimum assay sensitivity. The assay zone for the determination of analyte is prepared by employing in an appropriate assay solution, usually buffered, the unknown sample, which may have been subject to prior treatment, the chemiluminescer labeled reagent and the quencher labeled reagent (includes poly(ligand analog)-polylabel), and as appropriate ligand or antiligand.

The presence of antiligand or ligand in combination with a predetermined amount of antiligand in the assay medium controls the degree to which the quencher comes within quenching distance of the chemiluminescer.

There are four basic variations in the preparation of the quencher and chemiluminescer reagents. The four variations are:

(1) chemiluminescer conjugated to ligand as chemiluminescer labeled ligand and quencher conjugated to receptor as quencher labeled antiligand;

(2) quencher conjugated to ligand as quencher labeled ligand and chemiluminescer conjugated to receptor as chemiluminescer labeled antiligand; and (3) chemiluminescer conjugated to receptor as chemiluminescer labeled antiligand and quencher conjugated to receptor as quencher labeled antiligand.

(4) chemiluminescer conjugated to ligand as chemiluminescer labeled ligand and quencher conjugated to ligand as quencher labeled ligand.

With the first two combinations, when the reagents are combined, the quencher will be in quenching distance of the chemiluminescer. The presence of analyte, either ligand or antiligand, will serve to reduce the amount of energy transfer between the chemiluminescer and quencher by diminishing the number of quencher molecules within quenching distance of the chemiluminescer. In the third combination, a polyepitopic ligand (includes poly(ligand analog)) must be added for either antiligand or monoepitopic ligand as analyte. Where the ligand is polyepitopic, increased quenching will be observed as the concentration of the polyepitopic ligand increases to a maximum quenching, followed by decreased quenching as the concentration of polyepitopic ligand continues to increase. Thus, a biphasic response is obtained, so that one must know on which portion of the curve one is operating in order to obtain a discrete result. By contrast, with poly(ligand analog), the presence of monoepitopic ligand will serve to diminish quenching. With receptor as analyte, increasing concentrations of receptor will also serve to diminish quenching.

Where the chemiluminescer and the quencher are both conjugated to ligand, an assay for either ligand or polyvalent antiligand may be performed. Where the assay is for ligand, the two label-conjugates are employed in conjunction with antiligand which brings the chemiluminescer and quencher together into quenching distance of each other. The addition of ligand reduces the amount of chemiluminescer and label which are within quenching distance. For the determination of antiligand the two label-conjugates are employed. With increasing amounts of antiligand, there will be a decrease of chemiluminescence to a minimum and then an increase as the concentration of antiligand increases. If one is uncertain as to which portion of the biphasic curve is involved, one or more sample dilutions will indicate the particular concentration.

It should be understood, that in referring to quenching, all that is intended is that there be transfer of energy from the chemiluminescer to the quencher. The result of this transfer will be that light of a single or range of wavelengths which might otherwise have been emitted by the chemiluminescer will be transferred to the quencher, which may then fluoresce, emitting light of a higher wavelength than the energy absorbed. Depending upon the quantum efficiency of emission of the chemiluminescer, the efficiency of energy transfer from the chemiluminescer to the quencher, and the quantum efficiency of emission of the quencher, as well as the wavelength range which is monitored, one may observe greater or lesser amounts of light due to the quenching. Therefore, when referring to quenching, it is not intended that there necessarily be a diminution of the signal which is observed. In fact, if one is observing the light emitted by the quencher, increasing quenching will result in an increasingly large signal.

A special situation exists with small haptens, those of from about 125 to 2000 molecular weight. With these haptens a substantially reduced chemiluminescence can be achieved i.e. quenching without quencher bonded to receptor, particularly where the receptor is an antibody. While the reduction in signal will not be as great as when quencher is conjugated to receptor, a sufficient reduction may be achieved to have an acceptable assay. Except for using receptor without quencher, the assay will be performed in the same manner, reading the light emitted by the chemiluminescer.

In carrying out the assay, an aqueous medium will normally be employed. Other polar solvents may also be employed, usually oxygenated organic solvents of from one to six, more usually from one to four carbon atoms, including alcohols, ethers and the like. Usually, these cosolvents will be present in less than about 40 weight percent, more usually in less than about 20 weight percent.

The pH for the medium will usually be in the range from about 5 to 12, more usually in the range from about 7 to 10, and when enzymes are employed as part of the chemiluminescence source, 7 to 9. Various buffers may be used to achieve the desired pH and maintain the pH during the determination. Illustrative buffers include borate, phosphate, carbonate, Tris, barbital and the like. The particular buffer employed is not critical to this invention, but in individual assays, one buffer may be preferred over another.

Moderate temperatures are normally employed for carrying out the assay and usually constant temperatures during the period of the assay will be employed. The temperatures will normally range from about 10° to 50° C., more usually from about 15° to 40° C.

The concentration of analyte which may be assayed will generally vary from about $10^{-4}$ to $10^{-15}$ M, more usually from about $10^{-6}$ to $10^{-13}$ M. Stated another way, the concentration ranges of interest will generally be from about $10^{-3}$ to $10^{-14}$ g/ml.

In addition to the concentration range of analyte of interest, considerations such as whether the assay is qualitative, semi-quantative or quantitative, the equipment employed, and the characteristics of the reagents will normally determine the concentration of the reagents. While the concentration of analyte will determine the range of concentrations of the other reagents, normally to optimize the sensitivity of the assay, individual reagent concentrations will be determined empirically. Since the binding constant and binding profile of receptors will vary, for example, with antibodies from bleed to bleed, each new batch of antibodies may require different concentration ratios for the different reagents.

Normally, for mono- and polyepitopic ligand analytes, the concentration of antiligand based on binding sites will be about equal to the minimum concentration of interest based on binding sites and not more than about 50 times the maximum concentration of interest based on binding sites, usually about 1 to 10 times, and more usually about 1 to 3, times the maximum concentration of interest based on binding sites.

For polyepitopic ligand receptor analytes, the equivalent ratios of labeled ligand or ligand to receptor analyte will generally be in the range of about 0.01 times the minimum concentration of interest and not more than about 100 times the maximum concentration of interest based on binding sites. The labeled receptor employed in conjunction with the labeled ligand or ligand will generally be present in from about 0.01 to 100 times the concentration of ligand or labeled ligand based on binding sites.

For polyepitopic ligand analytes, where labeled ligand is employed, the concentration of labeled ligand will generally be not less than about $10^{-4}$, more usually not less than about $10^{-2}$ times the minimum concentration of interest and usually in the range of about equal to the minimum concentration of interest and not exceeding about the maximum concentration of interest. The ratio of labeled receptor will generally be not less than about 0.1 times the concentration of labeled ligand based on binding sites and not greater than about 100 times the concentration of labeled ligand based on binding sites.

For monoepitopic ligand analytes and monoepitopic ligand receptor analytes, when employing labeled ligand (includes poly(ligand analog)-label), the concentration of labeled ligand based on binding sites will usually be not less than $10^{-4}$ times the minimum concentration of interest, more usually not less than $10^{-2}$ times the minimum concentration of interest and usually in the range of about the minimum concentration of interest to the maximum concentration of interest. When poly(ligand analog) is employed with labeled antiligand, the concentration of poly(ligand analog) will fall within the same ranges as indicated for the labeled ligand and the concentration of antiligand has been indicated previously.

The order of addition of the various reagents may vary widely, depending upon whether an equilibrium or rate measurement is involved, the nature of the reagents, the rate at which equilibrium is achieved between the ligand and antiligand, and the nature of the chemiluminescence source. Where the chemiluminescence source has a plurality of components, with one of the components being a label, the chemiluminescence can be initiated at any time by the addition of the other components of the chemiluminescence source. In those situations where the chemiluminescence source involves more than one component, the labeled reagents and the unknown may be combined simultaneously, followed by the addition of the other components of the chemiluminescence source. Alternatively, one could combine the analyte with the labeled antiligand, followed by the addition of labeled ligand, as appropriate, followed by the addition of the remaining components of the chemiluminescence source. The various additions may be interrupted by incubation. In those instances where the chemiluminescence source is a single component, normally the labeled receptor will be combined with the analyte, followed by the addition of the labeled ligand, as appropriate.

Depending on the mode employed, equilibrium or nonequilibrium, the rate of binding of the antiligand to ligand and labeled ligand and the relative concentrations of the ligand, labeled ligand and labeled antiligand, one or more incubation steps may be involved. Normally, times between additions may vary from a few seconds to many hours, usually not exceeding 16 hrs, more usually not exceeding 6 hrs. Usually, incubation times will vary from about 0.5 min to 1 hr, more usually from about 0.15 min to 30 min. Since the ultimate result will be dependent upon the result obtained with standard(s) treated in substantially the same manner, and when possible in the identical manner the particular mode and periods of time are not critical, so long as significant reproducible differentiations are obtained with varying concentrations of analyte.

Depending upon the choice of assay protocol, the equipment employed and the concentration of analyte involved, assay volumes may be as small as about 1 $\mu$l, more usually being about 25 $\mu$l, and will usually not exceed 5 ml, more usually not exceeding 2 ml.

The assay measurement will depend upon counting the quanta of light emitted from the assay medium. Various instruments may be used, such as scintillation counters, photocells or the like, which are capable of measuring light at a single or over a range of wavelengths.

Materials

The primary components in the subject assay for analyte, which may or may not be employed in every case are: labeled ligand (includes poly(ligand analog)-label); labeled antiligand; ligand; antiligand; and additional components as required for the chemilumiinescence source.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
   $\alpha_1$-glycoprotein
$\alpha_1$X-Glycoprotein
Thyroxin-binding globulin
Inter-$\alpha$-trypsin-inhibitor
Gc-globulin
   (Gc 1-1)
   Gc 2-1)
   (Gc 2-2)
Haptoglobin
   (Hp 1-1)
   (Hp 2-1)
   (Hp 2-2)
Ceruloplasmin
Cholinesterase
$\alpha_2$-Lipoprotein(s)
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II Immunoglobulin G
  (IgG) or γG-globulin
Mol. formula:
  $\gamma_2 \kappa_2$ or $\gamma_2 \lambda_2$
Immunoglobulin A (IgA)
  or γA-globulin
Mol. formula:
  $(\alpha_2 \kappa_2)^n$ or $(\alpha_2 \lambda_2)^n$
Immunoglobulin M
  (IgM) or γM-globulin
Mol. formula:
  $(\mu_2 \kappa_2)^5$ or $(\mu_2 \lambda_2)^5$
Immunoglobulin D (IgD)
  or γD-Globulin (γD)
Mol. formula:
  $(\delta_2 \kappa_2)$ or $(\delta_2 \lambda_2)$
Immunoglobulin E (IgE)
  or γE-Globulin (γE)
Mol. formula:
  $(\epsilon_2 \kappa_2)$ or $(\epsilon_2 \lambda_2)$
Free K and γ light chains
Complement factors:
C'1
  C'1q
  C'1r
  C'1s
C'2
C'3
  $\beta_1 A$
  $\alpha_2 D$
C'4
C'5
C'6
C'7
C'8
C'9

Important blood clotting factors include:

| BLOOD CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone
  (parathromone)
Thyrocalcitonin
Insulin
Glucagon
Relaxin
Erythropoietin
Melanotropin
  (melanocyte-stimulating hormone; intermedin)
Somatotropin
  (growth hormone)
Corticotropin
  (adrenocorticotropic hormone)
Thyrotropin
Follicle-stimulating hormone
Luteinizing hormone
  (interstitial cell-stimulating hormone)
Luteomammotropic hormone
  (luteotropin, prolactin)
Gonadotropin
  (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)
CRF, LRF, TRF, Somatotropin-RF,
GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrhoeae | Polysaccharide |
| Corynebacterium diphtheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Eryipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby | Polysaccharide |
| Salmonella pullorum Shigella dysenteriae Shigella flexneri | Polysaccharide |
| Shigella sonnei | Crude, polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria

*Corynebacterium diptheriae*

Pneumococci

*Diplococcus pneumoniae*

Streptococci

*Streptococcus pyogenes*
*Streptococcus salivarus*

Staphylococci

*Staphylococcus aureus*
*Staphylococcus albus*

Neisseriae

*Neisseria meningitidis*
*Neisseria gonorrheae*

---

Enterobacteriaciae

*Escherichia coli*
*Aerobacter aerogenes*    } The coliform bacteria
*Klebsiella pneumoniae*
*Salmonella typhosa*
*Salmonella choleraesuis*  } The Salmonellae
*Salmonella typhimurium*
*Shigella dysenteriae*
*Shigella schmitzii*
*Shigella arabinotarda*
*Shigella flexneri*        } The Shigellae
*Shigella boydii*
*Shigella Sonnei*
Other enteric bacilli
*Proteus vulgaris*
*Proteus mirabilis*        } Proteus species
*Proteus morgani*
*Pseuomonas aeruginosa*
*Alcaligenes faecalis*
*Vibrio cholerae*
Hemophilus-Bordetella group
*Hemophilus influenzae,*   H. ducreyi
                           H. hemophilus
                           H. aegypticus
                           H. paraiufluenzae

*Bordetella pertussis*

---

Pasteurellae

*Pasteurella pestis*
*Pasteurella tulareusis*

Brucellae

*Brucella melitensis*
*Brucella abortus*
*Brucella suis*

Aerobic Spore-forming Bacilli

*Bacillus anthracis*
*Bacillus subtilis*
*Bacillus megaterium*
*Bacillus cereus*

Anaerobic Spore-forming Bacilli

*Clostridium bolulinum*
*Clostridium tetani*
*Clostridium perfringens*
*Clostridium novyi*
*Clostridium septicum*
*Clostridium histolyticum*
*Clostridium tertium*
*Clostridium bifermentans*
*Clostridium sporogenes*

Mycobacteria

*Mycobacterium tuberculosis hominis*
*Mycobacterium bovis*
*Mycobacterium avium*
*Mycobacterium leprae*
*Mycobacterium paratuberculosis*

Actinomycetes (fungus-like bacteria)

*Actinomyces israelii*
*Actinomyces bovis*
*Actinomyces naeslundii*
*Nocardia asteroides*
*Nocardia brasiliensis*

The Spirochetes

*Treponema pallidum*
*Treponema pertenue*
*Treponema carateum*
*Borrelia recurrentis*
*Leptospira icterohemorrhagiae*
*Leptospira canicola*
*Spirillum minus*
*Streptobacillus moniliformis*

Mycoplasmas

*Mycoplasma pneumoniae*

Other pathogens

*Listeria monocytogenes*
*Erysipelothrix rhusiopathiae*
*Streptobacillus moniliformis*
*Donvania granulomatis*
*Bartonella bacilliformis*

Rickettsiae (bacteria-like parasites)

*Rickettsia prowazekii*
*Rickettsia mooseri*
*Rickettsia rickettsii*
*Rickettsia conori*
*Rickettsia australis*
*Rickettsia sibiricus*
*Rickettsia akari*
*Rickettsia tsutsugamushi*
*Rickettsia burnettii*
*Rickettsia quintana*

Chlamydia (unclassifiable parasites bacterial/viral)
Chlamydia agents (naming uncertain)

---

Fungi

*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
*Mucor corymbifer (Absidia corymbifera)*
*Rhizopus oryzae*
*Rhizopus arrhizus*         } Phycomycetes
*Rhizopus nigricans*
*Sporotrichum schenkii*
*Fonsecaea pedrosoi*
*Fonsecaea compacta*
*Fonsecaea dermatitidis*
*Cladosporium carrionii*

| Fungi |
| --- |
| *Phialophora verrucosa* |
| *Aspergillus nidulans* |
| *Madurella mycetomi* |
| *Madurella grisea* |
| *Allescheria boydii* |
| *Phialosphora jeanselmei* |
| *Microsporum gypseum* |
| *Trichophyton mentagrophytes* |
| *Keratinomyces ajelloi* |
| *Microsporum canis* |
| *Trichophyton rubrum* |
| *Microsporum andouini* |

Viruses

Adenoviruses

Herpes viruses

Herpes simplex
Varicella (Chicken pox)
Herpes Zoster (Shingles)
Virus B
Cytomegalovirus

Pox Viruses

Variola (smallpox)
Vaccinia
Poxvirus bovis
Paravaccinia
Molluscum contagiosum

Picornaviruses

Poliovirus
Coxsackievirus
Echoviruses
Rhinoviruses

Myxoviruses

Influenza (A, B, and C)
Parainfluenza (1-4)
Mumps Virus
Newcastle Disease Virus
Measles Virus
Rinderpest Virus
Canine Distemper Virus
Respiratory Syncytial Virus
Rubella Virus

Arboviruses

Eastern Equine Eucephalitis Virus
Western Equine Eucephalitis Virus
Sindbis Virus
Chikugunya Virus
Semliki Forest Virus
Mayora Virus
St. Louis Encephalitis Virus
California Encephalitis Virus
Colorado Tick Fever Virus
Yellow Fever Virus
Dengue Virus

Reoviruses

Reovirus Types 1-3

Hepatitis

Hepatitis A Virus
Hepatitis B Virus

Tumor Viruses

Rauscher Leukemia Virus
Gross Virus
Maloney Leukemia Virus

Allergens

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, detromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids; isoquinoline alkaloids; quinoline alkaloids; which includes quinine and quinidine; diterpene alkaloids, their derivatives and metabolites.

The next group of drugs includes steroids, which includes the estrogens, gestrogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethyl stilbestrol.

The next group of drugs is lactams having from 5 to 6 annular members, which include the barbiturates, e.g. phenobarbital and secobarbital diphenylhydantoin, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, C, D, E and K.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucelotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propanolol, griseofulvin, butyrophenones, antihistamines, anticholinergic drugs, such as atropine, their metabolites and derivatives.

The next group of compounds is amino acids and small peptides which include polyiodothyromines e.g.

thyroxine, and triiodothyronine, oxytocin, ACTH, angiotensin, gentamycin, met- and leu-enkephalin their metabolites and derivatives.

Metabolites related to diseased states include spermine, galactose, phenylpyruvic acid, and porphyrin type 1.

Among pesticides of interest are polyhalogenated biphenyls, phosphaee esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 600,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Label

Quencher

The quencher molecule is a chromophore which absorbs light in the wavelength band emitted by the chemiluminescer. Preferably, the quencher will absorb light at a wavelength close to the emission maximum wavelength of the chemiluminescer. What is desired, is that there be a high efficiency of energy transfer when the quencher is in relatively close juxtaposition to the chemiluminescer source. Normally, the quencher will absorb light at greater than about 350 Å, more usually at greater than about 400 Å. Various chromophores which may be employed as quenchers include the xanthene dyes, which include the fluoresceins derived from 3,6-dihydroxy-9-phenylxanthhydrol and rosamines and rhodamines, derived from 3,6-diamino-9-phenylxanthhydrol. The rhodamines and fluoresceins have a 9-o-carboxyphenyl group and are derivatives of 9-o-carboxyphenylxanthhydrol.

These compounds are commercially available with substituents on the phenyl group which can be used as the site for bonding or as the bonding functionality. For example, amino and isothiocyanate substituted fluorescein compounds are available.

Other dyes which may be used as quenchers include 3-phenyl-7-isocyanatocoumarin, acridines, such as 9-isothiocyanatoacridine and acridine orange; N-(p-(2-benzoxazolyl)phenyl)maleimide; benzoxadiazoles, such as 4-chloro-7-nitrobenzo-2-oxa-1,3-diazole and 7-(p-methoxybenzylamino)-4-nitrobenzo-2-oxa-1,3-diazole; stilbenes, such as 4-dimethylamino-4'-isothiocyanatostilbene and 4-dimethylamino-4'-maleimidostilbene; N,N'-dioctadecyloxacarbocyanine p-toluenesulfonate; pyrenes, such as 8-hydroxy-1,3,6-pyrenetrisulfonic acid, and 1-pyrenebutyric acid; merocyanines e.g. merocyanine 540, rose bengal, 2,4-diphenyl-3(2H)-furanone; cyanines; anthiaquinones; porphyrines; triarylmethanes; as well as other readily available dyes which are capable of quenching. These dyes, either have active functionalities for conjugation or such functionalities may be readily introduced.

It should further be noted that the absorption and emission characteristics of the dye may vary from being free in solution and being bound to a protein or ligand. Therefore, when referring to the various wavelength ranges and characteristics of the dyes, it is intended to indicate the dyes as employed and not the dye which is unconjugated and characteristized in an arbitrary solvent. In the area of overlap between the chemiluminescer and quencher, it is desirable that the quencher should have a high transition probability.

Finally, the "blue fluorescent proteins" and/or "green fluorescent proteins" normally associated with certain bacterial luciferases e.g. the luciferase from Photobacterium fisheri, may also be used as a quencher.

Chemiluminescer

The chemiluminescent source may have a single component or a plurality of components, usually two or three components. While it is feasible that there be a single molecule which is thermally labile and on decomposition chemiluminesces, such as certain dioxetanes, for a number of reasons the use of these molecules will not be commercially practical. While one could prepare reagents and maintain them at sufficiently low temperatures, so that the rate of decomposition was acceptably slow and then warm the reagent immediately prior to use, such technique will generally be inconvenient, even though it does have some parallel with radioimmunoassay. Therefore, for the most part, the chemiluminescence source will have at least two components and the major portion of the discussion will be directed to this situation.

For purposes of convenience, the chemiluminescence source will be divided into two categories: those which do not involve the intermediacy of enzyme catalysis; and those which do involve enzyme catalysis.

Considering chemiluminescence sources which do not involve enzyme catalysis, only those sources can be employed which chemiluminesce under conditions which either do not inhibit the binding of the receptor to the ligand, or degrade the receptor and ligand at an unacceptable rate during the period of measurement. While ordinarily chemiluminescent sources which are dependent upon nonaqueous solvents and strong basic conditions, greater than pH11, will not be useful, techniques can be employed involving rapid injection or flow techniques where the modulated emission is substantially completed before the protein is denatured and significant disassociation occurs. After injection of base, one would observe a burst of light which could be measured.

A diverse number of families of compounds have been found to provide chemiluminescence under a variety of conditions. One family of compounds are 2,3-dihydro-1,4-phthalazinediones. The most popular compound is luminol, which is the 5-amino compound. Other members of the family include the 5-amino-6,7,8-trimethoxy and the dimethylamino[ca]benz analog. These compounds can be made to luminesce with alkaline hydrogen peroxide or calcium hypochlorite and base. Another family of compounds are the 2,4,5-triphenylimidazoles, with lophine as the common name for the parent product. Chemiluminescent analogs include para-dimethylamino and -methoxy substituents.

The next group of chemiluminescent compounds are indolen-3-yl hydroperoxides, precursors thereto and derivatives thereof.

The next group of compounds are the bis-9,9'-biacridinium salts, of which lucigenin, N,N'-dimethyl-9,9'-biacridinium dinitrate is illustrative. These compounds chemiluminesce upon combination with alkaline hydrogen peroxide.

The next group of compounds are acridinium salts which are substituted in the 9 position. Particular substituents are carboxylic esters, particularly the aryl esters, acyl substituents, particularly benzoyl, and cyano. Alkaline hydrogen peroxide is employed to induce chemiluminescence.

Another group of compounds are various acyl peroxy esters and hydroperoxides, which may be formed in situ in combination with compounds such as 9,10-diphenylanthracene.

Another source of chemiluminescence is hydroperoxides e.g. tetralin hydroperoxide in combination with metal complexes, particularly porphyrins and phthalocyanines, where the metals are iron and zinc.

Preferred systrms are those which provide a satisfactory quantum efficiency of emission from the chemiluminescer at a pH at or below 11, preferably at or below 10, and, furthermore, rely on a catalyst which may be conjugated to a member of the immunological pair. Where the system does not involve the catalyst, the compound which decomposes with the emission of light will be conjugated to the member of the immunological pair. In these circumstances, the number of chemiluminescent molecules with be limited to those which are conjugated.

The next group of compounds are based on chemiluminescers which chemiluminescence under enzymatic catalysis. Primarily, there are two groups of enzymatically catalyzed chemiluminescers. The first group are those compounds which chemiluminesce in combination with alkaline hydrogen peroxide. By employing a peroxidase e.g. horseradish peroxidase or catalase, in combination with hydrogen peroxide and the chemiluminescer, chemiluminescence can be achieved. Illustrative systems include 2,3-dihydro-1,4-phthalazinediones.

The second enzymatic source of chemiluminescence is based on luciferins and their analogs and luciferases.

Labeled Ligand

The ligands may be divided into two categories, haptens which are generally from 125 to 5,000 molecular weight, more usually from about 125 to 2,000 molecular weight and more particularly from about 125 to 1,000 molecular weight and antigens which will generally be not less than about 2,000 molecular weight, usually not less than about 5,000 molecular weight and when present as part of a cell, virus, chromosome or the like, may have molecular weights in excess of 10,000,000. For the most part, the antigens of diagnostic interest will generally be less than about 1,000,000 molecular weight, more usually less than about 600,000 molecular weight and more particularly will range from about 10,000 to 350,000 molecular weight.

The label will either be a quencher, which will generally be from about 125 to 1,000 molecular weight or a component of the chemiluminescent source, which may be a small molecule of from about 125 to 1,000 molecular weight or a large molecule, such as an enzyme or hemin which will range from about 10,000 to 250,000 molecular weight, more usually from about 10,000 to 150,000 molecular weight.

Depending upon the nature of the ligand and the label, the character of the labeled ligand will vary widely. The first labeled ligand which will be considered is the quencher-hapten reagent. Since both molecules are small, there will normally be a 1 to 1 ratio with a relatively short linking group between the two parts of the quencher-hapten.

Where an antigen is involved, there may be one or more quenchers conjugated to the antigen. Generally, there will be at least about one quencher molecule per 100,000 molecular weight, more usually at least about one quencher molecule per 50,000 molecular weight and generally not more than about one quencher molecule per 1,000 molecular weight, more usually not more than about one quencher molecule per 2,000 molecular weight. With antigens in the range of about 10,000 to 300,000 molecular weight, the number of quencher molecules will generally be in the range of about 2 to 30, more usually from about 2 to 20, and preferably from about 2 to 16.

Where the component of the chemiluminescent source which is conjugated is a small molecule, that is having a molecular weight in the range of about 125 to 1,000, there will normally be a one to one ratio of chemiluminescer component to hapten in the chemiluminescer-hapten reagent. With antigens, the number of small chemiluminescent components will generally be not less than 1, usually not less than 1 per 100,000 molecular weight, more usually not less than 1 per 50,000 molecular weight and generally not more than 1 per 1,000 molecular weight, more usually not more than 1 per 2,000 molecular weight.

Where antigens and large (over 10,000) chemiluminescent source components are involved, the ratios will vary widely, with either a plurality of the chemiluminescent source component bonded to the antigenic ligand or a plurality of ligands bonded to the chemiluminescent source component. Generally, the ratio of antigen to chemiluminescent source component will be in the range of about 0.05 to 20, more usually in the range of about 0.01 to 10, where both the chemiluminescent source and the antigen have molecular weights in the range of about 10,000 to 300,000.

The nature of the linking group will vary widely depending upon the particular materials which are being joined. Generally, linking groups will vary from a bond to about 20 atoms in the chain which are carbon, oxygen, nitrogen and sulfur, particularly carbon, oxygen and nitrogen where the nitrogen is substituted solely with carbon or is neutral, where it may be substituted with both carbon and hydrogen e.g. amido. A wide variety of linking groups are set forth in U.S. Pat. No. 3,817,837, which disclosure is incorporated herein by reference.

Where a poly(ligand analog)-label is involved, a hub nucleus may be employed, which is normally a water soluble polymer and conveniently a poly(amino acid) or polysaccharide.

Usually, the hub nucleus will be from about 25,000 to 600,000 molecular weight, more usually from about 30,000 to 300,000 molecular weight. Enzymes to which ligand analog may be linked will generally vary from about 15,000 to 300,000 molecular weight. The same linking groups as discussed above may be employed for linking the label and the ligand analog to the hub nucleus or enzyme.

The functionalities involved in the linking will normally include alkylamine, amide, amidine, thioamide, urea, thiourea and guanidine. Illustrative functionalities involved in linking are carboxylic acids in conjuction with diimides, mixed anhydrides with carbonate monoesters, aldehydes in conjunction with reductants e.g. borohydrides, imidoesters, active carboxylic esters e.g.

N-hydroxy succinimide or p-nitrophenyl, isocyanates, isothiocyanates, active halide and the like.

Labeled Receptor

The receptor may be labeled with either the quencher or the chemiluminescent source component. Where the label is a small molecule of about 125 to 1,000 molecular weight, there will usually be at least one label per receptor and not more than about one per 1,500 per molecular weight of receptor more usually not more than about one label per 2,500 molecular weight of receptor and preferably not more than about one label per 5,000 molecular weight of receptor. Where the receptor is an antibody, IgG, the number of labels will generally be from about 2 to 20, more usually from about 2 to 12. Where the label is a macromolecule, that is of from about 10,000 to 300,000 molecular weight, there will generally be from about 1 to 10 labels, more usually from about 1 to 6 labels.

The manner of conjugation to the receptor has been indicated previously.

Kits

In carrying out the subject assays, in order to obtain reproducible results, it is desirable that the critical reagents be provided in predetermined ratios, so as to optimize the sensitivity of the assay. In the assay for ligand, the critical reagents include labeled ligand, including poly(ligand analog)-label and labeled receptor. In the assay for receptor, ligand may also be a critical reagent. Besides the desire to have the critical reagents in predetermined proportions, it is frequently desirable that ancillary materials, such as buffer, stabilizers and the like, be included with critical reagents, so that dry powders or concentrates may be diluted to form assay solutions directly, avoiding the necessity of weighing the various materials.

In the kit, the reagents will be provided in relative proportions, so as to substantially optimize the sensitivity of the assay to the concentration range of interest. In addition, included with one or both of the reagents may be buffer, inert proteins, such as albumins, stabilizers, such as sodium azide and the like. Desirably, the reagents are provided as dry powders, particularly with labeled polyepitopic ligand and receptors, where these materials may be lyophilized.

The following examples are offered by way of illustration and not by way of limitation.

EXPERIMENTAL

All temperatures not otherwise indicated are in centigrade. All percents or parts not otherwise indicated are by weight except for mixtures of ligands which are by volume.

EXAMPLE 1

Conjugation of horseradish peroxidase to human gamma-globulin (hIgG)

The method employed is described in Nakane and Kawaoi, J. Hist. Cyto. 22 (12), 1084-1091 (1974).

In 1 ml of 0.3 M sodium bicarbonate buffer, pH 8.1, was introduced 6 mg horseradish peroxidase (HRP) and 100 µl of a 1% aqueous solution of 2,4-dinitro-1-fluorobenzene and the mixture incubated for 1 hr. The mixture was then dialzyed against 0.01 M sodium carbonate, pH 9.5 for 2 hrs followed by dialysis against 0.3 M sodium bicarbonate buffer, pH 8.1.

An approximately 1.5 ml solution of the HRP material prepared above was added to 1 ml 0.4 M sodium periodate and the mixture allowed to stand for 45 min at room temperature. To the solution was then added 25 µl of 0.32 M aqueous ethylene glycol, the mixture allowed to stand for 1 hr, followed by dialysis for 2 hrs in a collodion bag apparatus against 0.01 M sodium carbonate, pH 9.5. The residue in the dialysis bag was then combined with 5 mg hIgG and the mixture allowed to stand for 1 hr. At this time, 15 mg sodium borohydride was added, the mixture allowed to stand for 1.25 hrs at room temperature and the product then dialyzed overnight in a collodion bag apparatus against PBS, pH 7. The residue in the dialysis bag was then chromatographed on Sephadex G-200 with 0.01 M PBS, pH 7. Fractions were collected, with fraction 7 spectrophotometrically found to be $2.5 \times 10^{-7}$ M hIgG and $4.95 \times 10^{-7}$ M HRP.

EXAMPLE 2

Conjugation of fluorescein to anti(hIgG)

Into a vial fitted with stirring bar was introduced 5 mg lyophilized rabbit anti(hIgG) (Miles Laboratories, Lot 18, Code 64-155) and the mixture dissolved in 0.5 ml aqueous sodium phosphate, pH 8.0 and the pH adjusted to 9 with aqueous sodium carbonate buffer. A solution of 0.3 mg fluorescein isothiocyanate in 0.3 ml DMF was added over about 40 secs with vigorous stirring and the mixture stirred for 60 min. At the end of this time, the reaction mixture was chromotographed on a Sephadex (G-25) column and the fractions collected. A fraction was obtained having 2.4 mg/ml of anti(hIgG) with a fluorescein/anti(hIgG) ratio of about 5 to 1.

In order to demonstrate the subject invention, the following assay was carried out at room temperature. The solutions employed were a 1.86 mg/ml aqueous solution of hIgG, a 0.023 mg/ml solution of the fluorescein-anti(hIgG) conjugate (prepared above) and a $2.5 \times 10^{-8}$ M solution of the HRP-hIgG conjugate. In addition, 100 µl each of aqueous solutions $10^{-3}$ M luminol and $10^{-5}$ M hydrogen peroxide were also added. The following table indicates the amounts of materials added and the results as read as counts per 0.1 min at different times from the time of mixing.

TABLE

| hIgG µl | Fluorescein-anti(hIgG) µl | HRP-hIgG µl | Counts per 6 sec from time of mixing in min. (in thousands) | | |
|---|---|---|---|---|---|
| | | | 5 | 15 | 60 |
| 0 | 0 | 25 | 23.3 | 38.3 | 56.8 |
| 1 | 5 | 25 | 27.2 | 41.1 | 60.8 |
| 2.5 | 5 | 25 | 34.9 | 50.3 | 71.3 |
| 5 | 5 | 25 | 36.8 | 44.7 | 81.7 |
| 10 | 5 | 25 | 49.8 | 66.0 | 78.9 |

The apparatus employed was a β-Mate Scintillation Counter, non-coincidence mode.

It is evident from the above results, that a standard curve can be prepared for determining the amount of an analyte in an assay medium. The method is quite simple in that the reagents may be rapidly combined and a reading taken within a very short period of time. In addition, after about 0.5 hour the readings stabilize, so that the timing of the reading becomes less critical.

The subject assay provides a convenient means for determining quantitatively a wide variety of analytes. In addition, the method allows for multiplication of the signal, by employing a catalytic system, either enzymatic or nonenzymatic, which provides a plurality of events for each molecule of analyte present in the medium. In addition, the method avoids the problems of light scatter and protein absorption and emission interfering with the results which are determined.

Although the foregoing invention has been described in some detail by way of illustration and example for purposes of clarity of understanding, it will be obvious that certain changes and modifications may be practiced within the scope of the appended claims.

What is claimed is:

1. A diagnostic kit for use in a method for determining in an assay solution, the presence of an analyte in a sample suspected of containing said analyte, said analyte being a member of an immunological pair consisting of ligand and antiligand, said ligand having at least one epitopic site and said antiligand being capable of specifically binding to said epitopic site of said ligand; wherein a light emitting reciprocal pair are employed as labels, said light emitting reciprocal pair consisting of a chemiluminescence source having at least one component and a quencher capable of quenching the light emitted by said chemiluminescence source without collision, said labels being conjugated to members of said immunological pair to form a chemiluminescence label conjugate and a quencher label conjugate, and wherein in said assay solution the amount of quencher brought within quenching distance of said chemiluminescence source is related to the amount of analyte in said assay medium; said kit comprising in relative amount to substantially optimize said method, said chemiluminescence label conjugate and said quencher labeled conjugate.

2. A kit according to claim 1, wherein said chemiluminescence source component is an enzyme.

3. A kit according to claim 2, wherein said enzyme is conjugated to said ligand.

4. A kit according to claim 1, wherein said chemiluminescence source component and said quencher dye are both conjugated to antiligand.

* * * * *